(12) United States Patent
Khosla et al.

(10) Patent No.: US 6,548,485 B2
(45) Date of Patent: Apr. 15, 2003

(54) STABLE ANTITUMOR DRUG

(75) Inventors: Chaitan Khosla, Palo Alto, CA (US); Akihiko Fujie, Ibaraki (JP)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/854,257

(22) Filed: May 11, 2001

(65) Prior Publication Data
US 2002/0049168 A1 Apr. 25, 2002

Related U.S. Application Data

(60) Provisional application No. 60/203,731, filed on May 12, 2000.

(51) Int. Cl.$^7$ .......................... A61K 31/70; C07H 17/08
(52) U.S. Cl. .......................................... 514/28; 536/7.1
(58) Field of Search .............................. 536/7.1; 514/28

(56) References Cited

PUBLICATIONS

Hayakawa et al., J. Am. Chem. Soc. (1998) 120:3524–3525.
Kim et al., Antibiot. (1997) 50:628–630.

*Primary Examiner*—Elli Peselev
(74) *Attorney, Agent, or Firm*—Morrison & Foerster LLP

(57) ABSTRACT

A stable derivative of apoptolidin retains sufficient potency to be useful as an antitumor drug.

9 Claims, 2 Drawing Sheets

STABLE ANTITUMOR DRUG

CROSS-REFERENCE TO RELATED APPLICATIONS

This application claims priority under 35 U.S.C. § 119(e) to U.S. provisional application Serial No. 60/203,731 filed May 12, 2000, the contents of which are incorporated herein by reference.

STATEMENT OF RIGHTS TO INVENTIONS MADE UNDER FEDERALLY SPONSORED RESEARCH

This work was supported by a grant from the National Institutes of Health (2 R01-CA 66736).

TECHNICAL FIELD

The invention relates to cancer treatment, specifically to an improved stable anticancer agent which is a derivative of apoptolidin.

BACKGROUND ART

A microbial product, apoptolidin, has been isolated from Nocardiopsis sp. which selectively sensitizes cancer cells to apoptosis. (Kim, J. W., et al., *Antibiot.* (1997) 50:628–630; Hayakawa, Y., et al., *J. Am. Chem. Soc.* (1998) 120:3524–3525.) While apoptolidin shows considerable potency in its ability to induce apoptosis selectively, it is unstable under alkaline conditions, and, unfortunately, under neutral, physiological conditions. The present invention provides a more stable derivative of apoptolidin which retains the selective apoptosis inducing activity of apoptolidin.

DISCLOSURE OF THE INVENTION

The invention is directed to a stabilized derivative of apoptolidin which lacks the oleandrose and olivomycose sugars. The derivative is stable under physiological conditions and a potent selective antitumor agent.

Thus, in one aspect, the invention is directed to a compound of the formula

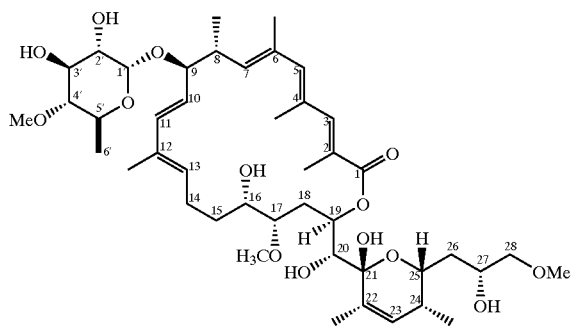

and the pharmaceutically acceptable esters and/or ethers thereof.

In other aspects, the invention is directed to pharmaceutical or veterinary compositions of the compounds of formula 1 and to methods to treat tumors by administering the compound of formula 1 or a pharmaceutical composition thereof. "Treatment" includes both therapeutic and prophylactic effects. In still other aspects, the invention is directed to a method to synthesize the compound of formula 1 by conversion from apoptolidin and optional esterification and on conversion to either forms.

MODES OF CARRYING OUT THE INVENTION

Figure 1:
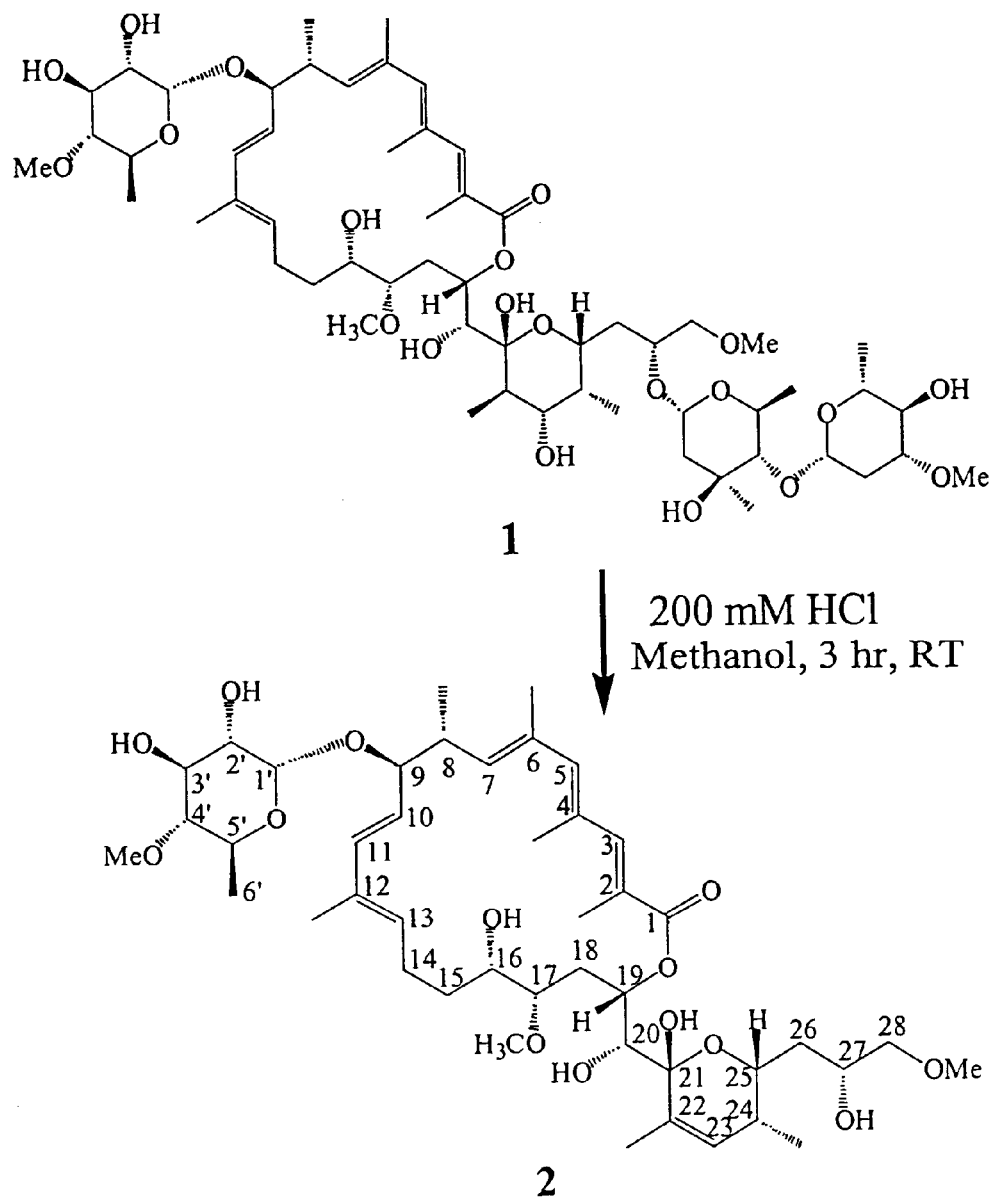
FIG. 1 shows a scheme for the conversion of apoptolidin to the invention compound.

The invention is directed to the compound of formula 1 and its lower alkyl or substituted alkyl esters and ethers. The compound of formula 1 per se is preferred. The alkyl esters are formed in a conventional manner from the compound of formula 1 by treatment with suitable acyl derivatives. The acyl moiety may contain 1–6 carbons, and may optionally be substituted by hydroxy or methoxy. Five hydroxyl groups are available for esterification; the invention includes compounds in which one or more of these groups are esterified.

The invention compounds also include the ethers formed from one or more of the five available hydroxyl groups; ethers may be formed from the relevant alkyl halides, which halides contain 1–2C. As with respect to the ester derivatives, one, two, or more of the hydroxyls may be in the form of ethers. Mixed esters and ethers are also included within the scope of the invention. Synthesis of these derivatives is conventional.

The compound of formula 1 also contains chiral centers; the compounds of the invention include stereoisomers of the compound of formula 1 and mixtures of stereoisomers thereof. As used herein, the "compound of formula 1" includes the ethers, esters and various stereoisomeric forms. The "compound of formula 1 per se" refers to the structure as shown.

The compounds of the invention are formulated into suitable compositions for pharmaceutical or veterinary use for the treatment of various tumors. In particular, tumors of the breast, colon, prostate, ovaries, lung, and metastatic forms thereof, including cancers residing in the bone can be treated in this manner. Exemplary malignancies also include lymphomas and other nonsolid tumors. The foregoing list is merely for illustration and should not be construed as limiting.

The compositions are those conventional for administration of, for example, antibiotics to humans and animals. Thus, the compositions may be suitable for oral administration, including tablets, capsules, syrups, and the like; for injection in physiologically compatible solutions; for mucosal administration wherein the composition contains surfactants; or for transdermal administration which typically includes penetrants. The compositions may contain liposomes or other carriers that facilitate the activity of the active ingredient. Sustained release compositions are also available. Pharmaceutical compositions in general are described in *Remington's Pharmaceutical Sciences*, latest edition, Mack Publishing Co., Easton Pa., the contents of which are incorporated herein by reference for a description of a variety of pharmaceutical compositions suitable for the compounds of the invention. Veterinary compositions are similar. The compositions may contain mixtures of the invention compounds and/or additional active ingredients.

The mode of administration and dosage levels will depend on the nature of the formulation, the condition of the subject, the judgment of the practitioner, and the nature of the tumor to be treated. Optimization of such parameters as dosage and route of administration are well within ordinary skill.

The compound of formula 1 can readily be prepared by treating apoptolidin in an alcoholic acid solution at ambient temperatures for several hours. The conditions of time and temperature may vary and optimal conditions for preparation of the compound of formula 1 from apoptolidin can be readily obtained by straightforward optimization techniques. The immediate product may be converted to the ester and/or ether forms.

Figure 2:
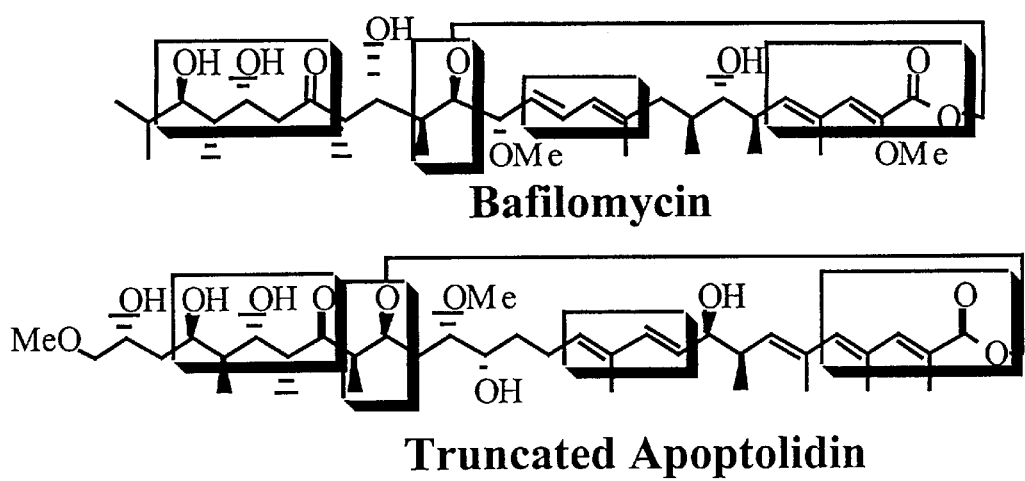
FIG. 2 shows a comparison of the invention compound with bafilomycin.

While not intending to be bound by any theory, applicants believe that the compound of the invention enhances apoptosis susceptibility by cancer cells by targeting vacuolar $H^+$-ATPases (V-ATPases). FIG. 2 shows the structural similarity between the parent compound apoptolidin and bafilomycin which is a known inhibitor of V-ATPases. Others have shown that the dienic system of the macrolide ring of bafilomycin is crucial to this bafilomycin activity while modifications to the hemiketal ring do not seem to be crucial. (Gagliardi, S., et al., *J. Med. Chem.* (1998) 41:1883–1893.) The compound of formula 1, similarly, contains a dienic macrolide ring.

The following examples are intended to illustrate but not to limit the invention.

EXAMPLE 1

Preparation of Formula 1

Apoptolidin was obtained by fermentation of Nocardiopsis sp. as described by Kim, J., et al. (supra) and treated with 0.2 M HCl in methanol for 3 hours at room temperature.

The reaction mixture was subjected to preparative reverse-phase HPLC with a full linear gradient from 100% water to 100% acetonitrile in 60 minutes at 15 ml/min on a Beckman C18 column (21.2 mm×15 cm).

The fraction containing the product of formula 1 was obtained in 12% yield.

The structure of the product was confirmed by NMR and mass spectrometry. The disappearance of oleandrose and olivomycose was established by disappearance of peaks corresponding to these residues from COSY and HMQC spectra. The molecular formula was confirmed by FAB-MS to be $C_{44}H_{68}O_{13}$ [m/z 827.4667(M+Na)$^+$11.0 mmu] consistent with the compound of formula 1 less a molecule of water.

EXAMPLE 2

Activity of the Invention Compound

Activity was measured by FACS staining for annexin V and by MTT assay.

A. Mouse B Cell Lymphoma

The mouse B cell lymphoma cell line LYas was incubated with apoptolidin in a compound of formula 1 per se for 6 hours. The treating compounds were removed and the cells were stained with annexin V-Cy5PE for 15 minutes and washed 3 times. Cells were analyzed on the FACSAN and the percentage of annexin V positive cells was quantified. The $IC_{50}$ of the compound of formula 1 was 10 μM; the $IC_{50}$ of apoptolidin was 100 nM.

B. Breast Carcinoma

The breast carcinoma cell line MCF-7 was tested in 96-well plates in triplicate. Dilutions of apoptolidin or the compound of formula 1 per se were added to the wells for 120 hours. MTT was then added to the wells at a final concentration of 0.5 mg/ml. The supernatant was removed and the crystals dissolved in 40 mM HCl and isopropanol. The plates were scanned on a microplate reader at 595 nm. The $IC_{50}$ of the compound of formula 1 was 10 μM; the $IC_{50}$ of apoptolidin was 90 nM.

It is seen that while still exhibiting an antitumor effect, the effect is less than that of apoptolidin.

EXAMPLE 3

Stability of the Compound of Formula 1

Stability was monitored by an analytical reverse phase HPLC using a Beckman C18 column (4.6 mm×25 cm). Stability was analyzed in this manner at pH 4, 7 and 10, both for apoptolidin and the compound of formula 1 per se. At pH 4, apoptolidin retained its structure for 24 hours; the compound of formula 1 for at least 28 hours when observation was terminated.

At pH 7, apoptolidin immediately equilibrated to an unknown compound and decomposed with a half-life of about 5 hours. The compound of formula 1 remained intact for at least 28 hours. At pH 10, apoptolidin decomposed almost immediately, and the compound of formula 1 was intact after 28 hours.

What is claimed is:

1. The compound of the formula

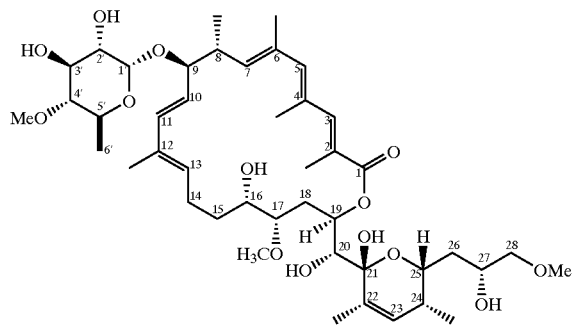

or ethers (1–2C) or esters (1–6C) thereof.

2. The compound of claim 1 which is of the formula

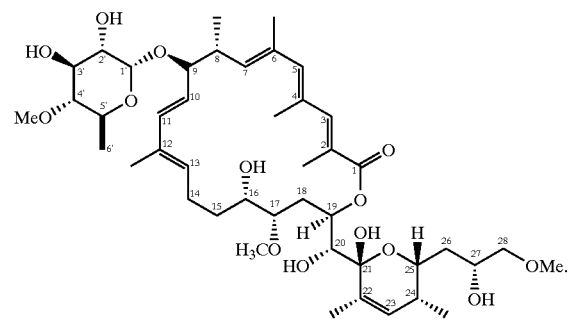

3. A pharmaceutical composition comprising as active ingredient the compound of claim 1, along with at least one pharmaceutically acceptable carrier.

4. A pharmaceutical composition comprising as active ingredient the compound of claim 2, along with at least one pharmaceutically acceptable carrier.

5. A method to treat a malignant tumor in a subject which method comprises administering to a subject in need of such treatment a therapeutically effective amount of the compound of claim 1.

6. A method to treat a malignant tumor in a subject which method comprises administering to a subject in need of such treatment a therapeutically effective amount of the compound of claim 2.

7. A method to prepare the compound of claim 1 which method comprises treating apoptolidin with an inorganic acid in the presence of alcohol at ambient temperature for a time sufficient to effect the conversion of apoptolidin to the compound of formula 1 and optionally converting said compound of formula 1 to the ether or ester form.

8. The method of claim 5, wherein the malignant tumor is a lymphoma or breast carcinoma.

9. The method of claim 6, wherein the malignant tumor is a lymphoma or breast carcinoma.

* * * * *